(12) United States Patent
Lade

(10) Patent No.: US 6,719,701 B2
(45) Date of Patent: Apr. 13, 2004

(54) IMPLANTABLE SYNCOPE MONITOR AND METHOD OF USING THE SAME

(75) Inventor: Kipton P. Lade, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 10/059,678

(22) Filed: Jan. 28, 2002

(65) Prior Publication Data

US 2003/0144595 A1 Jul. 31, 2003

(51) Int. Cl.[7] .............................. A61B 5/02; A61N 1/18
(52) U.S. Cl. ....................... 600/485; 600/481; 600/483; 607/9; 607/23
(58) Field of Search ................................ 600/485, 486, 600/483, 500, 508, 509, 515, 300, 301; 607/1, 2, 9, 17, 18, 23

(56) References Cited

U.S. PATENT DOCUMENTS

| | | | |
|---|---|---|---|
| 5,331,966 A | 7/1994 | Bennett et al. | 128/696 |
| 5,441,525 A | 8/1995 | Shelton et al. | 607/23 |
| 5,501,701 A | 3/1996 | Markowitz et al. | 607/9 |
| 5,540,728 A | 7/1996 | Shelton et al. | 607/23 |
| 5,676,686 A | 10/1997 | Jensen et al. | 607/9 |
| 5,800,467 A | 9/1998 | Park et al. | 607/17 |
| 5,913,879 A | 6/1999 | Ferek-Petric et al. | 607/14 |
| 5,919,210 A | 7/1999 | Lurie et al. | 607/3 |
| 5,987,352 A | 11/1999 | Klein et al. | 600/509 |
| 5,991,661 A | 11/1999 | Park et al. | 607/19 |
| 6,049,735 A | 4/2000 | Hartley et al. | 607/9 |
| 6,078,834 A | 6/2000 | Lurie et al. | 607/3 |
| 6,155,267 A | 12/2000 | Nelson | 128/899 |

FOREIGN PATENT DOCUMENTS

| | | | |
|---|---|---|---|
| EP | 0 959 945 B1 | 5/1996 | A61N/1/365 |

OTHER PUBLICATIONS

Krahn MD, Andrew D., et al.; "Final Results From a Pilot Study With an Implantable Loop Recorder to Determine the Etiology of Syncope in Patients With Negative Noninvasive and Invasive Testing"; American Journal of Cardiology; vol. 82, pp: 117–119 (Jul. 1, 1998).

Medtronic Reveal® Plus Insertable Loop Recorder Brochure; pp: 1–10; publication date unknown.

Medtronic Reveal® Plus Insertable Loop Recorder Implant & Programming Guide; pp: 1–33; publication date unknown.

Medtronic 0866—114621; ILR Pilot Study[1]; pp: 27; publication date unknown.

Medtronic 0866—114621; Recurrent Syncope; pp: 16–26; publication date unknown.

Medtronic 0866—114621; Seizures⇆Syncope:Long–Term Monitoring; pp: 48; publication date unknown.

Medtronic 0866—114621; System Components; pp: 57; publication date unknown.

Medtronic 0866—114621; Implanting Reveal® Plus; pp: 65–66; publication date unknown.

Medtronic 0866—114621; Using the Activator; pp: 75; publication date unknown.

Medtronic 0866—114621; Patient Follow–up Checklist; pp: 76; publication date unknown.

Medtronic 0866—114621; Main Screen; pp: 78; publication date unknown.

*Primary Examiner*—Max F. Hindenburg
*Assistant Examiner*—Navin Natnithithadha

(57) ABSTRACT

An implantable monitor and method to acquire, store, and display physiological data for the diagnosis of vasovagal syncope or intermittent cardiac arrhythmias. Physiological data monitored preferably comprises heart rate, blood pressure, and body posture. Physiological signals are monitored until detection of an event that triggers the storage of data. A storage-triggering event may be a maximum or minimum heart rate or blood pressure, a dramatic change in heart rate or blood pressure, or a patient-activated signal. In one embodiment, confirmed detection of vasovagal syncope by the monitor causes a telemetric command to enable a syncope therapy. Storage of physiologic data is triggered by predetermined arrhythmia or syncope detection criteria and appropriate stimulation therapy for the detected condition may be enabled.

30 Claims, 7 Drawing Sheets

IMPLANTABLE SYNCOPE MONITOR AND METHOD OF USING THE SAME

CROSS-REFERENCE TO RELATED APPLICATIONS

This application is related to commonly-assigned, U.S. application Ser. No. 09/457,451, filed Dec. 8, 1999, titled "An AC/DC Multi Axis Accelerometer For Determining Patient Activity And Body Position," currently U.S. Pat. No. 6,466,821 and to U.S. application Ser. No. 09/543,832, filed Apr. 5, 2000, titled "System And Method For Prevention Of Recurrent Vasovagal Syncope Using Cardiac Pacing," currently abandoned both of which applications are incorporated herein by reference.

FIELD OF THE INVENTION

The present invention relates generally to an implantable medical device for monitoring physiological signals. More specifically, the present invention is directed at providing a device and method for storing physiological signals during episodes of syncope or cardiac arrhythmias for use in the diagnosis of syncope or intermittent arrhythmias.

BACKGROUND OF THE INVENTION

Syncope, or fainting, as a result of inadequate cerebral blood flow may be caused by a number of neurocardiogenic or cardiac-related factors. A common form of syncope is vasovagal syncope, a type of neurocardiogenic syncope, that is believed to be precipitated by a reflex of the vagal nerves of the left ventricle that causes hypotension and can be accompanied by a sudden drop in heart rate. Though normally not life-threatening, vasovagal syncope may have serious consequences on a patient's quality of life and can result in injury and hospitalization. Syncope as a result of underlying cardiac dysfunction is a more serious form since the cardiac-related cause may be a life-threatening cardiac illness or arrhythmia.

In many cases, the diagnosis of syncope is a challenge. Nearly half of all cases of syncope are estimated to remain unexplained. One difficulty in diagnosing the cause of syncope is due to the intermittent nature of syncope. A patient may experience a syncopal event only a few times a year making attempts to monitor the cause of syncope in a physician's office somewhat "hit-or-miss."

Commonly used tests for diagnosing syncope may include a head-up tilt table test, an electrophysiological study, 24 to 48-hour ECG monitoring in the form of a Holter monitor, or external event recorders which may be used to record ECG events over a period of several weeks. The limitation of electrophysiological studies and Holter monitoring is again the fact that syncopal episodes, and the cardiac rhythms associated with syncope, may be intermittent and infrequent and therefore entirely missed by short-term monitoring. Even external ECG event recorders that can monitor for several weeks may not provide a long enough period of data collection to record a syncopal event. Another limitation of external devices is patient compliance in keeping skin electrodes well attached and wearing the external unit at all times.

A tilt-table test is used to induce a syncopal event in a clinical setting. A patient lies supine on a table for a period of time after which the table is tilted upward. Vasovagal syncope is characterized by a sudden drop in heart rate and a decrease in blood pressure which can sometimes be induced by a change in position. Tilt-table tests, however, have been found to produce falsely positive results in many cases. False negative results may also be obtained leaving the diagnosis as unexplained. A tilt-table test unfortunately does not always provide reliable results.

The opportunity to diagnose vasovagal syncope or an arrhythmic cause of syncope exists during an actual, spontaneous syncopal event. At that moment, physiological events leading up to the syncopal event can be recorded and analyzed for a more conclusive diagnosis.

Vasovagal syncope can result from at least three types of vasovagal responses: 1) a cardioinhibitory response producing a sudden drop in heart rate, 2) a vasodepressor response producing a sudden drop in blood pressure, and 3) a mixed response with both cardioinhibitory and vasodepressor responses. Vasovagal syncope usually occurs when a patient is upright and gravitational effects impact venous flow back to the heart, further decreasing flow to the brain, precipitating the syncopal event. Therefore, accurate diagnosis and selection of the most effective treatment for vasovagal syncope would include monitoring of patient blood pressure and patient position as well as heart rate or ECG when syncope occurs, as is done during a tilt-table test.

Vasovagal syncope may be treated by pacing the heart at an elevated rate when bradycardia (slow heart rate) occurs or may be treated by administration of a pharmocologic agent. Accurate diagnosis of the cause of syncope is important in determining the proper treatment and preventing recurrent vasovagal syncope.

It would be desirable, therefore, to provide an implantable medical device capable of monitoring heart rate, blood pressure, and patient position for the purpose of diagnosing vasovagal syncope or intermittent cardiac arrhythmias. An implantable monitor could record these physiological signals when a spontaneous syncopal event occurs and could replace or enhance inconclusive tilt-table testing. Incorporating such monitoring capabilities in a device that is capable of treating vasovagal syncope would allow therapy to be applied immediately in response to detected physiological events that normally precede or occur with syncope.

SUMMARY OF THE INVENTION

The present invention addresses these needs by providing an implantable medical device capable of sensing a patient's ECG, heart rate, blood pressure, and body posture or position, for the purposes of diagnosing vasovagal syncope or intermittent cardiac arrhythmias. In one embodiment, the device functions as a monitor by collecting and storing data for later transmission to an external device.

The monitoring device includes an insulated housing with at least two electrodes for sensing heart rate that are incorporated in the housing surface but are electrically insulated from each other and the housing. Within the monitoring device housing, additional physiological sensors may be included, preferably a blood pressure sensor, which may be an infrared sensor, and a position sensor, which may be a three-dimensional accelerometer.

The monitoring device further includes a programmable control system for controlling the monitoring functions, such as recognizing events that will trigger the storage of sensor data; a data acquisition system for sampling and digitizing ECG and sensor signals; a memory for storing data; and a telemetry circuit for transmitting stored data to an external device. A magnet detection circuit may be included for detecting when a patient-held activation device is held over the implanted device so that data storage may be triggered manually the patient when he or she is feeling symptomatic.

In operation, a number of programmable events, or combination of events, may trigger the storage of sensor data such as: an upper heart rate limit, a lower heart rate limit, an upper blood pressure limit, a lower blood pressure limit, a dramatic change in heart rate, or a dramatic change in blood pressure. Upon a detected trigger event or a patient-activated trigger, heart rate or ECG, blood pressure, and body position or posture data may be stored for a predetermined period of time. Data is then downloaded to an external device and used to diagnose a physiologic condition of vasovagal syncope or ventricular bradycardia, tachycardia, or fibrillation.

In an alternative embodiment, the monitoring methods provided by the present invention for diagnosing vasovagal syncope are incorporated in an implantable cardiac stimulation device. The stimulation device includes, in addition to the components of the monitoring device, a set of leads for receiving cardiac signals and for delivering atrial and ventricular stimulation pulses; a set of sensing circuits comprised of sense amplifiers for sensing and amplifying the cardiac signals; and pulse generators for generating atrial and ventricular stimulation pulses. When vasovagal syncope or a cardiac arrhythmia is detected by the monitoring methods provided by the present invention, operating parameters controlling the stimulation device may be automatically adjusted in order to deliver stimulation to the heart in a way that prevents or treats syncope or the arrhythmia.

The present invention thus provides a device and method for monitoring physiological data for the diagnosis of syncope based on the monitoring techniques used in tilt-table testing with the advantage of recording diagnostic data when a spontaneous syncopal event occurs. Vasovagal syncope due to a hypotensive response with or without a bradycardia response may be diagnosed. Intermittent cardiac arrhythmias may also be diagnosed. Confirmed syncopal or arrhythmic events may be treated by enabling a therapy to be delivered by another device, or the same device when monitoring methods are incorporated in a cardiac stimulation device.

BRIEF DESCRIPTION OF THE DRAWINGS

The various features of the present invention and the manner of attaining them will be described in greater detail with reference to the following description, claims, and drawings, wherein reference numerals are reused, where appropriate, to indicate a correspondence between the referenced items, and wherein:

DETAILED DESCRIPTION OF THE PREFERRED EMBODIMENTS

The following description is of a best mode presently contemplated for practicing the invention. This description is not to be taken in a limiting sense but is made merely for the purpose of describing the general principles of the invention. In the description of the invention that follows, like numerals or reference designators will be used to refer to like parts or elements throughout.

The present invention is directed at providing a monitoring device and method for storing physiologic data for the purposes of diagnosing vasovagal syncope. An implantable monitor will thus be described in conjunction with FIGS. 1 and 2, in which methods provided by the present invention for acquiring and storing data may be implemented. It is recognized, however, that numerous variations of such a device exist in which the methods of the present invention could be implemented without deviating from the scope of the present invention.

Figure 1:
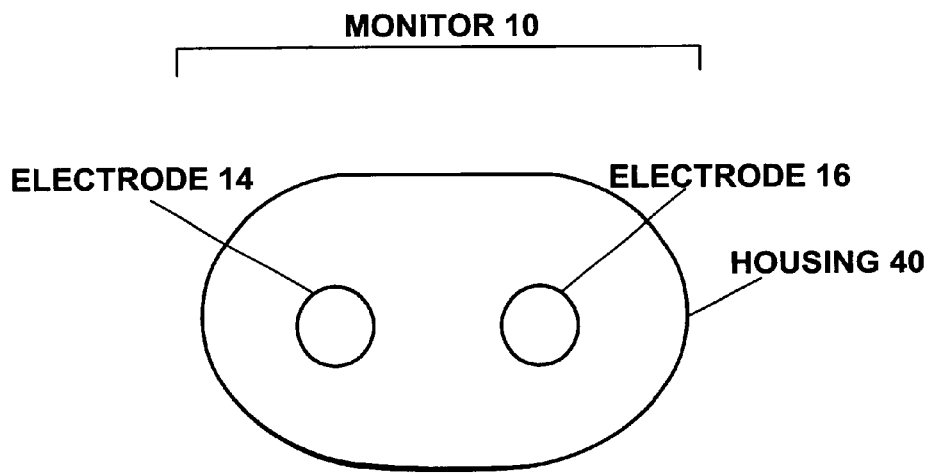
FIG. 1 is a simplified illustration of an implantable monitoring device for receiving, storing and transmitting physiological data for the purposes of diagnosing vasovagal syncope or intermittent cardiac arrhythmias.

FIG. 1 illustrates an external view of a monitor 10 to be implanted subcutaneously or submuscularly in a patient's body. The monitor 10 is encased in an insulated housing 40, also referred to as the "can" or "case." At least two sensing electrodes 14 and 16 are incorporated on the external surface of the housing 40 and are electrically insulated from each other and from the housing 40. The electrodes 14 and 16 may be used to monitor the patient's ECG to measure the patient's heart rate using electrodes 14 and 16, which changes as the ventricular mass depolarizes. The size and spacing of electrodes 14 and 16 are such that an adequate signal-to-noise ratio is obtained. The electrodes may be on the order of 1 cm or less in diameter and spaced approximately 1 to 4 cm apart. The electrodes are shown on one side of the monitor 10, but could also be located on opposite sides.

Figure 2:
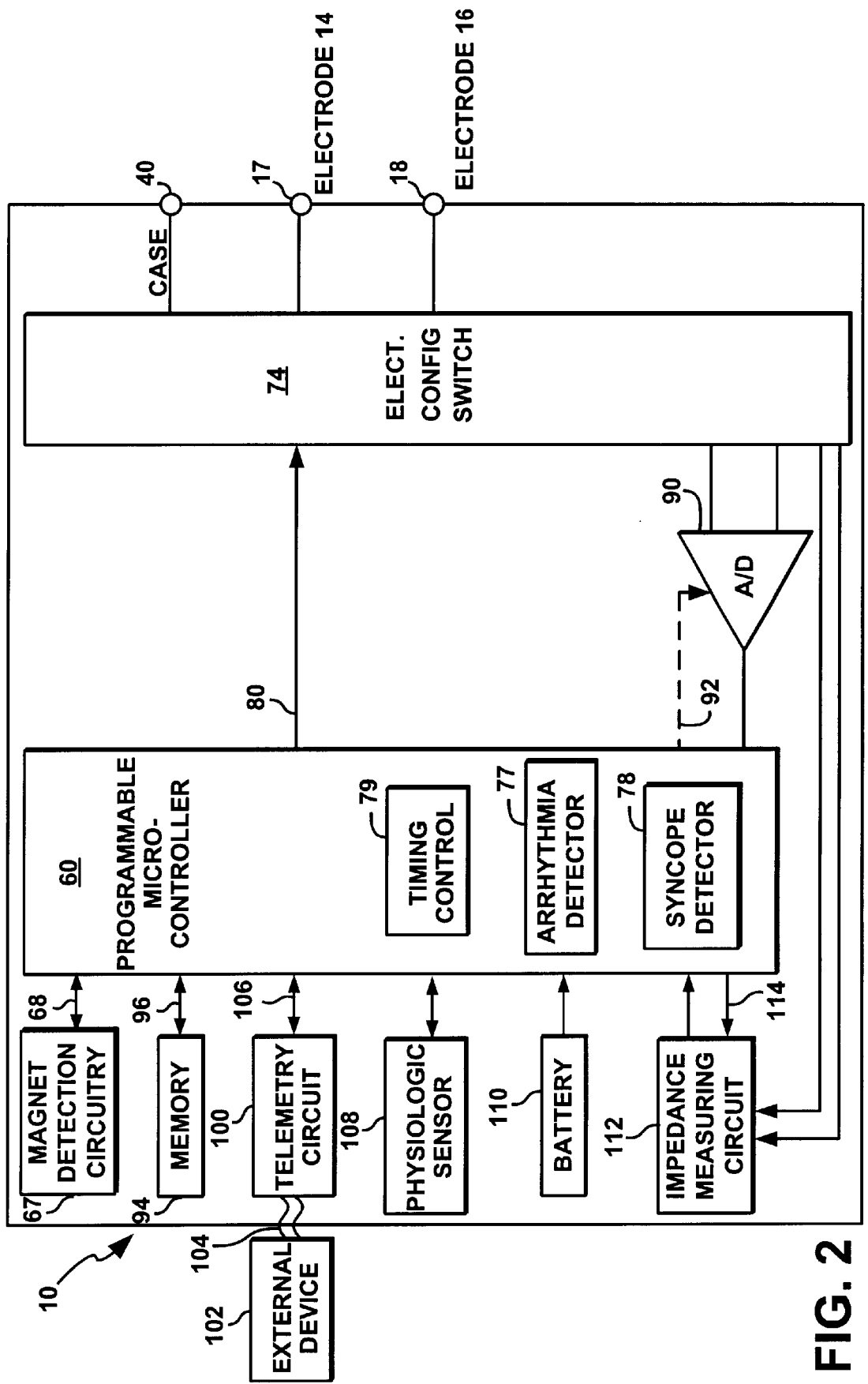
FIG. 2 is a functional block diagram of the monitoring device of FIG. 1, illustrating the basic elements that provide sensing, storage, and transmission of physiological signals important in diagnosing vasovagal syncope.

FIG. 2 illustrates a simplified block diagram of the monitor 10, which is capable of acquiring physiological signals important in diagnosing vasovagal syncope and storing the signals on a triggered basis. While a particular monitoring device is shown, this is for illustration purposes only, and one of ordinary skill in the art could readily duplicate, eliminate or disable the appropriate circuitry in any desired combination to provide a monitor capable of acquiring and storing a set of desired physiological signals for the purposes of diagnosing vasovagal syncope.

The housing 40 includes at least two terminals 54, and 52 (shown schematically and, for convenience, the names of the electrodes to which they are connected are shown next to the corresponding terminals) for connection to the sensing electrodes 14 and 16 incorporated on the surface of the monitor 10. To achieve ECG monitoring for monitoring heart rate, at least two terminals 17 and 18 are provided for connection to electrodes 14 and 16. The housing 40 may also be electrically connected by a terminal and function as a third electrode.

At the core of the monitor 10 is a programmable microcontroller 60 that controls the monitoring functions. The microcontroller 60 typically includes a microprocessor, or equivalent control circuitry, designed specifically for controlling the acquisition of physiologic data, and may further include RAM or ROM memory, logic and timing circuitry. Typically, the microcontroller 60 includes the ability to process or monitor input signals (data) as controlled by a program code stored in a designated block of memory. Any suitable microcontroller 60 may be used that carries out the functions described herein.

The microcontroller 60 includes a timing control circuit 79 that is used to control the timing of data acquisition and storage. One or more signals may be monitored by monitor 10, and, upon a specified triggering event, timing control circuitry 79 determines the beginning and ending time for storing monitored signals.

To acquire ECG, the switch 74 includes a plurality of switches for connecting the desired sensing electrodes to the inputs of a data acquisition system 90, which is depicted as an analog-to-digital (A/D) converter for simplicity of illustration. The data acquisition system 90 is configured to acquire ECG, convert the raw analog data into digital signals, and store the digital signals for processing and/or telemetric transmission to an external device 102. The data acquisition system 90 is coupled to the electrodes 14 and 16 and housing 40 through switch 74 to sample ECG across any pair of desired electrodes. The switch 74 thereby provides complete electrode programmability. Accordingly, the switch 74, in response to a control signal 80 from the microcontroller 60, determines the polarity of the sensing electrodes by selectively closing an appropriate combination of switches.

As illustrated in FIG. 2, the monitor 10 is shown to include an impedance measuring circuit 112 which is enabled by the microcontroller 60 by a control signal 114. The impedance measuring circuit is used by monitor 10 to measure body (or thoracic) impedance using electrodes 14 and 16 via switch 74 for the detection of a heart beat due to the change in impedance during ventricular depolarization. By measuring the bulk impedance of the body, the heart rate may be determined.

For arrhythmia detection, the microprocessor 60 includes an arrhythmia detector 77 that utilizes the ECG or heart rate signals received by data acquisition system 90 and impedance measuring circuit 112 for determining whether a rhythm is physiologic or pathologic.

As used herein "sensing" is reserved for the noting of an electrical signal, and "detection" is the processing of these sensed signals and noting the presence of an arrhythmia. The timing intervals between sensed heart beats are classified by the arrhythmia detector by comparing them to a predefined rate zone limit (e.g., bradycardia, normal, low rate ventricular tachycardia, high rate ventricular tachycardia, and fibrillation rate zones) and various other characteristics (e.g., sudden onset, stability, physiologic sensors, and morphology, etc.).

To achieve sensing of other physiological signal data useful in the diagnosis of vasovagal syncope, the monitor 10 includes a physiologic sensor 108, which may comprise one or more sensors.

In addition, a sensor of body position or posture, such as a three-dimensional accelerometer, is preferably included in physiologic sensor 108 for detecting when a patient is supine and when a patient is upright, for example, detecting when a change in position from a primarily vertical position to a more horizontal position occurs. For more details regarding the use of a three-dimensional accelerometer for detecting body position reference is made to U.S. patent application Ser. No. 09/457,451, supra. Blood pressure and body posture signals measured by physiologic sensor 108 are communicated to the microcontroller 60 for storage or further processing.

For vasovagal syncope detection, the microprocessor 60 includes a syncope detector 79 that analyzes the ECG or heart rate signal, the blood pressure signal, and the body posture signal to determine if vasovagal syncope is indicated. When vasovagal syncope is detected according to any of a number of predetermined criteria, storage of the physiological signal data (heart rate, blood pressure and body position) is triggered in order to record the syncopal episode for later analysis by a physician.

The microcontroller 60 is therefore coupled to a memory 94 by a suitable data/address bus 96 for writing and storing physiological data. The memory 94 is capable of storing large amounts of digitized physiological data in designated blocks of memory until such data is permanently downloaded and cleared by a physician. Memory 94 may also store the programmable operating parameters used by the microcontroller 60 that may be modified, as required, in order to customize the operation of the monitor 10 to suit the needs of a particular patient. Such operating parameters define, for example, the trigger events for storing physiological data and the time duration for acquiring and storing data.

Advantageously, stored physiologic signals obtained during detected syncopal or arrhythmic episodes may be transmitted by a telemetry circuit 100 through an established communication link 104 to an external device 102, such as a programmer or transtelephonic transceiver, for display and analysis by a clinician. In addition, the operating parameters of the monitor 10 may be non-invasively programmed into the memory 94 through the telemetry circuit 100. The telemetry circuit 100 is activated by the microcontroller 60 by a control signal 106. The telemetry circuit 100 allows transmission and status information relating to the operation of the monitor 10 (as contained in the microcontroller 60 or memory 94) to be sent to the external device 102 through the established communication link 104.

The monitor 10 is further equipped with a magnet detection circuitry 67, coupled to the microcontroller 60 via control signal 68. The magnet detection circuitry detects when a magnet is positioned over the monitor 10. A patient hand-held device, typically containing a magnet, may be held over the monitor 10 by the patient when he or she is feeling symptomatic. Detection of a magnet by the magnet detection circuitry 67 results in a signal to the microcontroller 60 that the physiological signal data acquired from physiologic sensor 108 and data acquisition system 90 should be written to memory 94. Magnet detection circuitry 67 may also be used to receive a signal indicating that the external device 102 is in place to receive or transmit data to the microcontroller 60 through the telemetry circuit 100.

The monitor 10 additionally includes a power source such as a battery 110 that provides operating power to all the circuits shown in FIG. 2.

Figure 3:
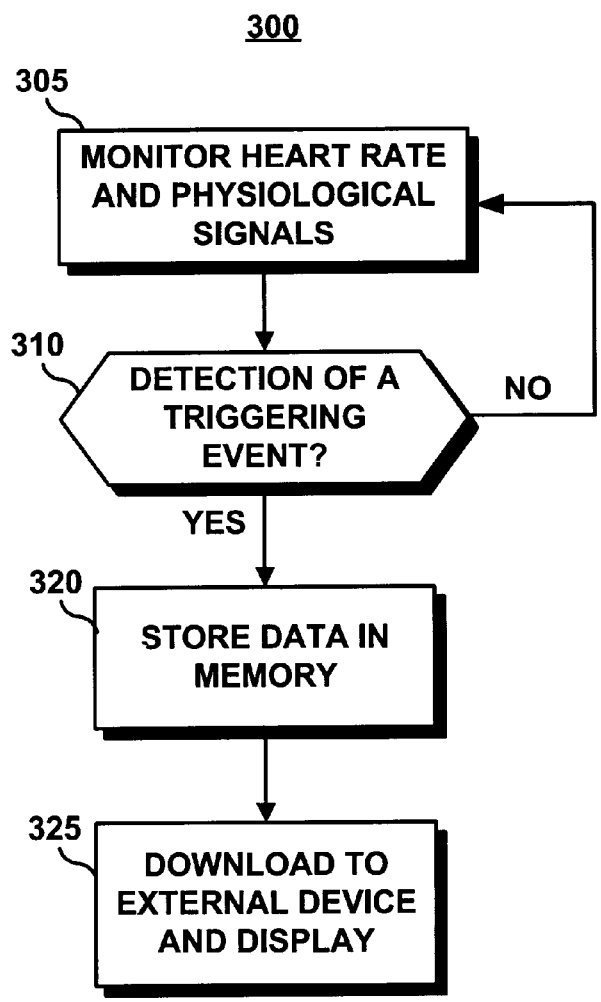
FIG. 3 is a flow chart providing an overview of the methods included in one embodiment of the monitoring device of FIG. 2 for monitoring physiological signals for the diagnosis of vasovagal syncope.

In FIG. 3, a flow chart is shown describing an overview of the operation and novel features implemented in one embodiment of the monitor 10 for monitoring physiological signals and storing data upon detection of a trigger event related to the diagnosis of vasovagal syncope. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the monitoring device. Those skilled in the art may readily write such a control program based on the flow charts and other descriptions presented herein.

At step 305, the monitor 10 is operating in a monitoring mode wherein the heart rate and any other physiological signals received by physiologic sensor 108 are acquired and stored temporarily in microprocessor 60. Data is temporarily stored in memory within microprocessor 60 until detection of a trigger event that will then cause the data to be written to memory 94 to be stored until it is downloaded to an external device 102. Preferably, on the order of, for example, 30 minutes of monitored data may be stored temporarily in microprocessor 60.

At decision step 310, the acquired signals are processed by syncope detector 79 for determining if a trigger event has occurred. A trigger event is the detection of a predefined level or change in one or more of the acquired signals that initiates a data storage episode. Trigger events may be preset or preferably programmable settings that are stored in memory 94 or microcontroller 60. For example, a trigger event may be the detection of a heart rate exceeding an upper rate limit, a heart rate lower than a lower rate limit, or a change in heart rate exceeding a given number of beats per minute. When blood pressure is also monitored, a trigger event may be the detection of a maximum or minimum blood pressure or dramatic decrease in blood pressure.

A trigger event may also be defined by the combination of changes in two or more physiological signals, for example a minimum heart rate and a dramatic decrease in blood pressure. In one embodiment, a patient may also trigger data storage by holding a hand-held device over the implanted monitor 10 when he or she feels symptomatic. As long as no trigger event is detected, physiologic data are continuously acquired and stored in microprocessor 60 with the oldest data being overwritten by the newest data.

Once a triggering event is detected at decision step 310, the heart rate and other physiologic data temporarily stored in microprocessor 60 are written to memory 94 at step 320. A physician may program the data to be stored upon a triggering event, which may include heart rate, ECG, blood pressure, and body posture. The data is stored for a predetermined amount of time before and following the triggering event. The storage period can be determined by, for example, the number of signals to be stored, the number of episodes to gather and/or the total available device memory.

At step 325, data stored in memory 94 is downloaded to an external device 102 and displayed for analysis by the physician. Data may also be downloaded transtelephonically from a distant location to a clinical center. Data may be displayed graphically or in a tabular format. Data may be displayed with respect to time on a common axis so that simultaneous events are easily identified.

Figure 4:
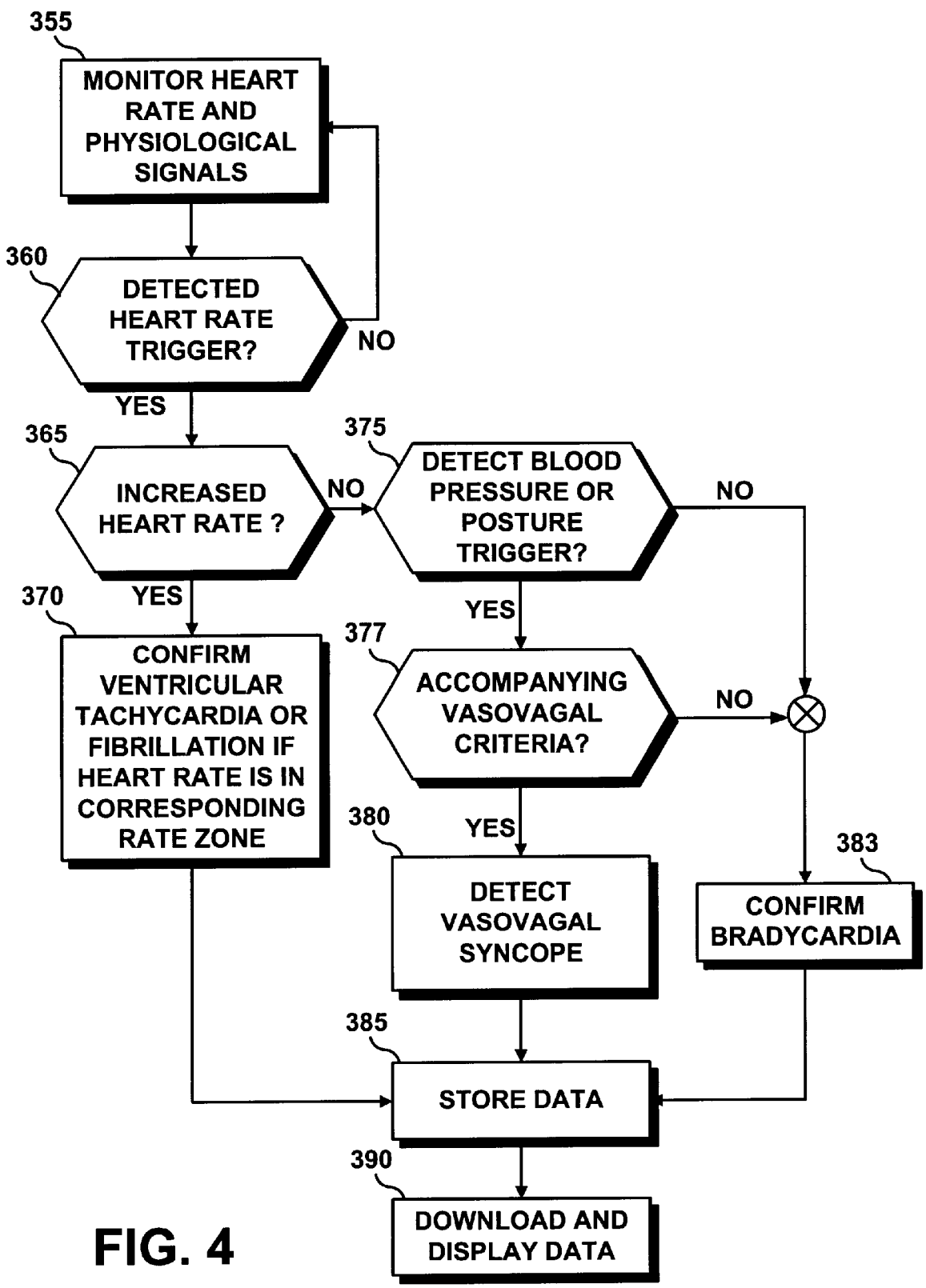
FIG. 4 is a flow chart depicting a method for the detection and diagnosis of vasovagal syncope or intermittent cardiac arrhythmias included in one embodiment of the monitoring device shown in FIG. 2.

The monitor 10 is capable of collecting data for the diagnosis of intermittent cardiac arrhythmias in addition to vasovagal syncope. The flow chart shown in FIG. 4 illustrates a method 350 that may be incorporated in monitor 10 for monitoring heart rate and other physiological signals for the detection and diagnosis of cardiac arrhythmias as well as vasovagal syncope.

At step 355, the heart rate and other physiological data, preferably blood pressure and body posture are monitored by microprocessor 60. At step 360, the arrhythmia detector 77 determines if a trigger event based on heart rate is detected. A heart rate trigger event could be a rate maximum, a rate minimum or a dramatic increase or decrease in rate. At decision step 365, the arrhythmia detector 77 determines if the heart rate trigger event represents an increase in heart rate or a decrease in heart rate.

If a decrease in heart rate has occurred, the syncope detector 79 analyzes other physiological signals at decision step 375 to determine if a syncopal or pre-syncopal condition is likely. Method 350 determines at decision step 377 if the decrease in heart rate is accompanied by one or more vasovagal criteria, such as decrease in blood pressure, a change in posture meeting, and/or any other physiological changes meeting predetermined criteria. If so, vasovagal syncope is detected at step 380. At step 385, the heart rate and other physiological data is written to memory 94 to store the events leading up to and during the syncopal event. At step 390, the data may be downloaded to an external device 102 for display.

However, if at decision step 377 method 350 determines that the decrease in heart rate is not accompanied by a vasovagal criterion that typically accompanies vasovagal syncope, it confirms the detection of bradycardia at step 383, and the heart rate and any other physiological data programmed to be stored are written to memory 94 at step 385. The data is then available to be downloaded to an external device 102 and displayed at step 390.

If an increased heart rate is detected at decision step 365, arrhythmia detector 77 determines if the heart rate falls into a tachycardia or fibrillation rate zone and confirms the tachycardia or fibrillation detection at step 370. At step 385, the heart rate data, and any other physiologic data programmed to be stored, are written to memory 94 for later downloading and display at step 390. Thus, method 350 allows monitor 10 to acquire, store and display data for the detection and diagnosis of vasovagal syncope and intermittent cardiac arrhythmias.

In one embodiment, the monitor 10 is capable of enabling a syncope therapy method or an arrhythmia therapy method in another implanted device by sending a telemetric communication signal to the other device whenever the monitor 10 determines that a syncopal or arrhythmia episode is imminent or already occurring. Another implanted device may be a cardiac stimulation device capable of delivering stimulation pulses to the heart chambers at a rate higher than the intrinsic rate for the treatment of syncope. Another implanted device may also be a drug pump capable of infusing a pharmacological agent to counteract the cardioinhibitory or vasodepressor responses associated with vasovagal syncope.

Figure 5:
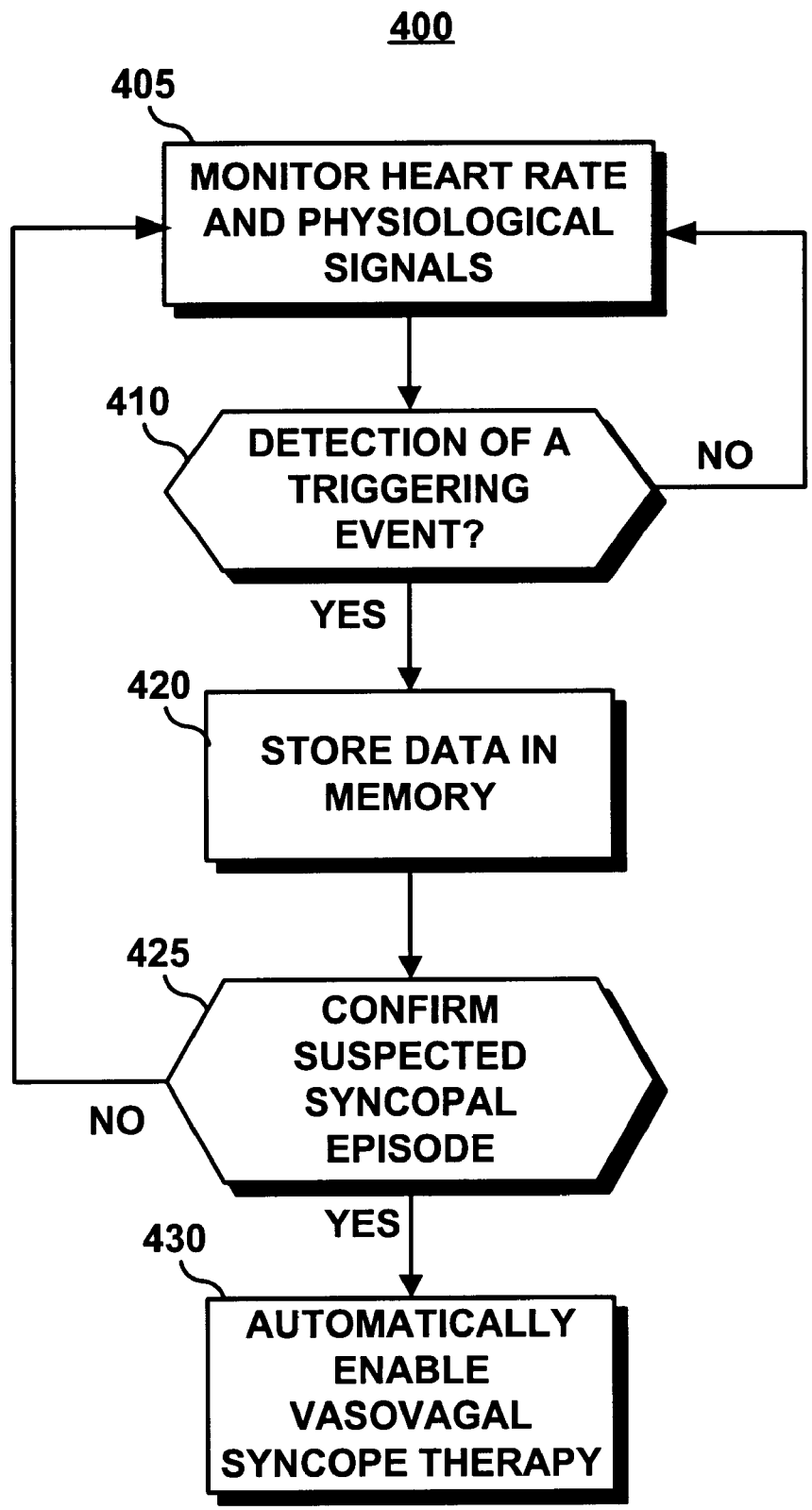
FIG. 5 is a flow chart depicting a method included in one embodiment of the monitoring device shown in FIG. 2 for enabling a vasovagal syncope therapy in a therapeutic device when vasovagal syncope is detected.

The flow chart shown in FIG. 5 provides an overview of the methods included in the monitor 10 for acquiring and storing data for the diagnosis of syncope and for enabling a syncope therapy in another device. At step 405, the monitor 10 monitors the heart rate and other physiologic signals until a storage-triggering event is detected at step 410. Data is then stored in memory 94 at step 420, and at step 425 the data and triggering event may be further analyzed in order to confirm that vasovagal syncope is suspected to be occurring or about to occur.

When monitoring heart rate, blood pressure and posture, any one or a combination of detected changes in these signals may be used as trigger events or for confirmation of vasovagal syncope at decision step 425. Combinations of changes that may be detected and the patient condition that is suspected to be associated with such changes are listed in TABLE 1. For example, detection of a sudden decrease in blood pressure may or may not indicate vasovagal syncope. A sudden decrease in blood pressure accompanied by an increase in heart rate above a predefined maximum normal rate range, with or without a change in posture, would indicate a ventricular tachycardia as shown in the first line of TABLE 1. A sudden decrease in blood pressure accompanied by a decrease in heart rate below a predefined minimum heart rate or a decrease in heart rate greater than a predefined maximum heart rate change, with or without a change in posture, does indicate vasovagal syncope. Likewise, a sudden drop in heart rate with a position change that may or may not be accompanied by a decrease in blood pressure may also indicate vasovagal syncope. However, an increase in heart rate with a simultaneous increase in blood pressure is considered a normal response as would be a decrease in heart rate with a rise in blood pressure.

TABLE 1

| HEART RATE | BLOOD PRESSURE | POSTURE | SUSPECTED CONDITION |
|---|---|---|---|
| Increase | Decrease | With or without change | Ventricular tachycardia |
| Increase | Increase | With or without change | Normal |
| Decrease | Decrease | With or without change | Vasovagal syncope |
| Decrease | Increase | With or without change | Normal |
| Decrease | With or without change | Position change | Vasovagal syncope |
| No change | Decrease | With or without change | Vasovagal syncope |

Detected changes in heart rate, blood pressure and posture and the associated patient condition are indicated.

If a suspected syncopal episode is confirmed at step 425, then, at step 430, monitor 10 sends a telemetric signal via telemetry circuit 100 to another device capable of receiving the signal and delivering a vasovagal syncope therapy in response.

The methods described heretofore for acquiring and storing physiologic data for the diagnosis of vasovagal syncope or intermittent cardiac arrhythmias included in the monitor 10 could alternatively be included directly in an implantable medical device capable of delivering a therapy for the treatment of vasovagal syncope or cardiac arrhythmias. For example, the monitoring methods included in monitor 10 may be included in an implantable cardiac stimulation device such as the one illustrated in FIG. 6.

Figure 6:
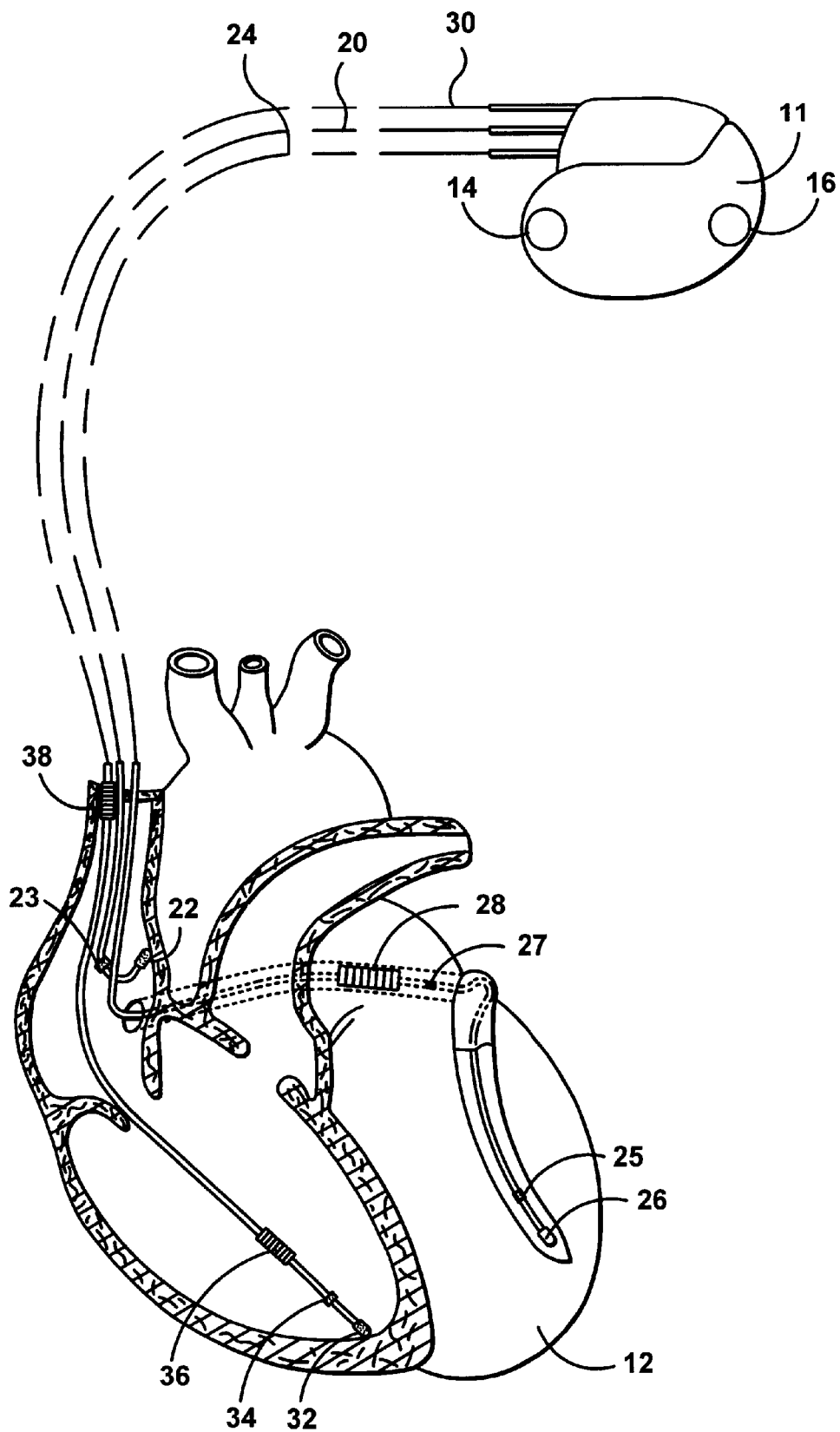
FIG. 6 is a simplified, partly cutaway view illustrating an implantable stimulation device in electrical communication with at least three leads implanted into a patient's heart for delivering multi-chamber stimulation and shock therapy in which a monitoring method for diagnosing vasovagal syncope is included.

A cardiac stimulation device 11 is shown in FIG. 6 to be in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 11 is coupled to an implantable right atrial lead 20 having at least an atrial tip electrode 22, which typically is implanted in the patient's right atrial appendage. The right atrial lead 20 may also have an atrial ring electrode 23 to allow bipolar stimulation or sensing in combination with the right atrial tip electrode 22.

To sense the left atrial and ventricular cardiac signals and to provide left-chamber stimulation therapy, the stimulation device 11 is coupled to a "coronary sinus" lead 24 designed for placement in the "coronary sinus region" via the coronary sinus ostium so as to place a distal electrode adjacent to the left ventricle and additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver left ventricular pacing therapy using: at least a left ventricular tip electrode 26 for unipolar configurations or in combination with left ventricular ring electrode 25 for bipolar configurations; left atrial pacing therapy using at least a left atrial ring electrode 27, and shocking therapy using at least a left atrial coil electrode 28.

The stimulation device 11 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the right atrium and/or superior vena cava. Accordingly, the right ventricular lead 30 is capable of receiving cardiac signals, and delivering stimulation in the form of pacing and shock therapy to the right ventricle.

Stimulation device 11 may also be equipped with self-contained electrodes 14 and 16 incorporated on the surface of the device 11 for sensing ECG signals for the determination of heart rate.

Figure 7:
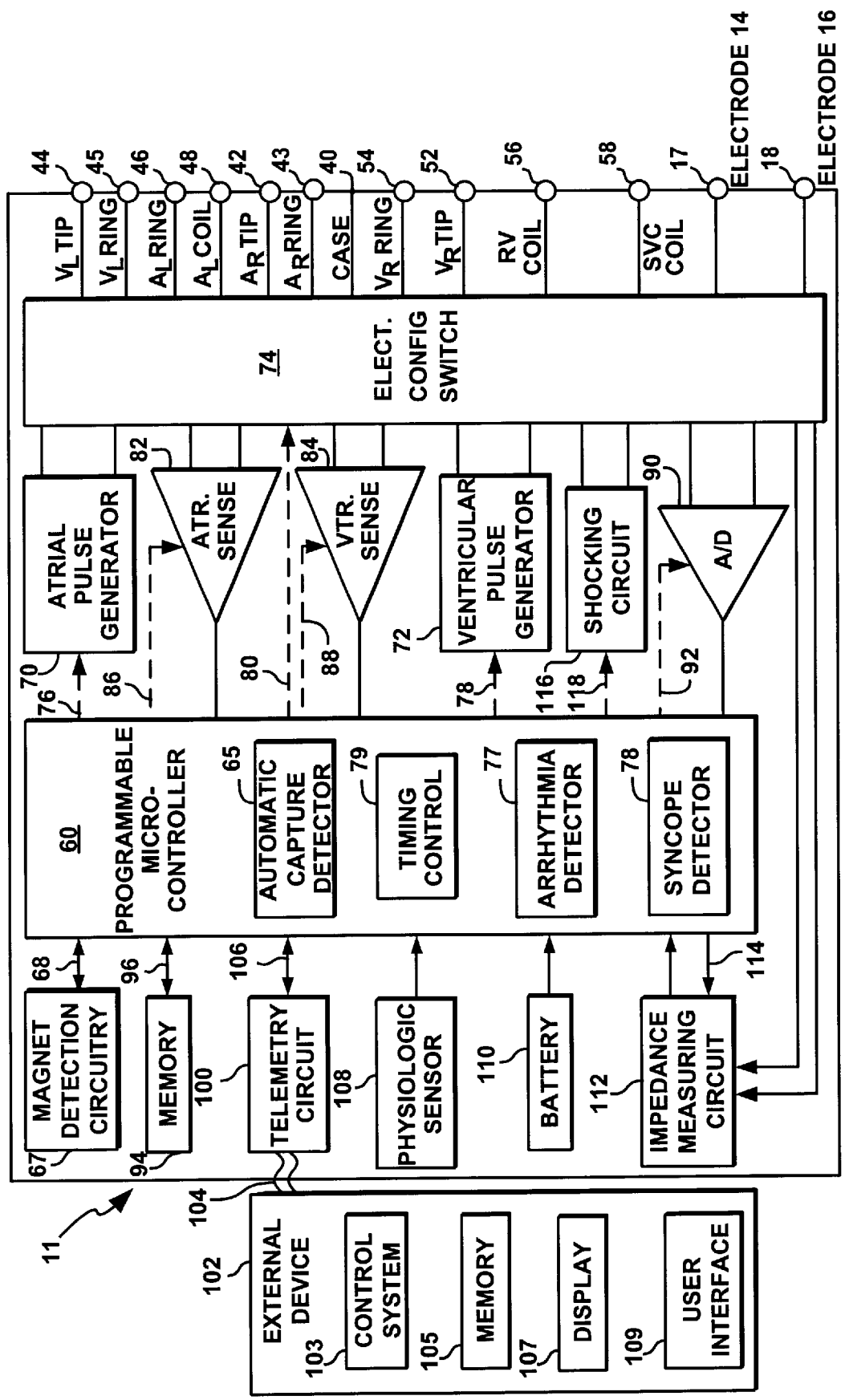
FIG. 7 is a functional block diagram of the multi-chamber implantable stimulation device of FIG. 6, illustrating the components that provide pacing stimulation, cardioversion, and defibrillation in four chambers of the heart.

FIG. 7 illustrates a simplified block diagram of the multi-chamber implantable stimulation device 11, which is capable of treating both fast and slow arrhythmias and vasovagal syncope with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The stimulation device 11 includes a housing 40 which is often referred to as "can", "case" or "case electrode", and which may be programmably selected to act as the return electrode for all "unipolar" modes. The housing 40 may further be used as a return electrode alone or in combination with one or more of the coil electrodes 28, 26, or 38, for defibrillation shocking purposes.

The stimulation device 10 further includes a connector having a plurality of terminals 17, 18 42, 43, 44, 45, 46, 48, 52, 54, 56, and 58 (shown schematically and, for convenience, the names of the electrodes to which they are connected are shown next to the corresponding terminals). As such, to achieve right atrial sensing and stimulation, the connector includes at least a right atrial tip terminal ($A_R$ TIP)

42 adapted for connection to the atrial tip electrode 22. The connector may also include a right atrial ring terminal ($A_R$ RING) 43 for connection to the right atrial ring electrode 23.

To achieve left chamber sensing, pacing, and shocking, the connector includes at least a left ventricular tip terminal ($V_L$ TIP) 44, a left ventricular ring terminal ($V_L$ RING) 45, a left atrial ring terminal ($A_L$ RING) 46, and a left atrial shocking coil terminal ($A_L$ COIL) 48, which are adapted for connection to the left ventricular tip electrode 26, the left ventricular ring electrode 25, the left atrial ring electrode 27, and the left atrial coil electrode 28, respectively.

To support right ventricular sensing, pacing and shocking, the connector further includes a right ventricular tip terminal ($V_R$ TIP) 52, a right ventricular ring terminal ($V_R$ RING) 54, a right ventricular shocking coil terminal (RV COIL) 56, and an SVC shocking coil terminal (SVC COIL) 58, which are adapted for connection to the right ventricular tip electrode 32, right ventricular ring electrode 34, the RV coil electrode 36, and the SVC coil electrode 38, respectively.

Terminals 17 and 18 are provided for connection to the sensing electrodes 14 and 16 incorporated on the surface of device 11 for detecting ECG signals for determining heart rate.

At the core of the stimulation device 11 is a programmable microcontroller 60 that controls the various modes of stimulation therapy. The microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. Any suitable microcontroller 60 may be used that carries out the functions described herein.

FIG. 7 illustrates an atrial pulse generator 70 and a ventricular pulse generator 72 that generate stimulation pulses for delivery by the right atrial lead 20, the right ventricular lead 30, and/or the coronary sinus lead 24 via a switch 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.), as well as to keep track of the timing of refractory periods, noise detection windows, evoked response windows, alert intervals, marker channel timing, etc.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, cross-chamber, etc.) by selectively closing the appropriate combination of switches.

Atrial sensing circuits 82 and ventricular sensing circuits 84 may also be selectively coupled to the right atrial lead 20, coronary sinus lead 24, and the right ventricular lead 30, through the switch 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch 74 determines the "sensing polarity" of the cardiac signal by selectively closing the appropriate switches. In this way, the clinician may program the sensing polarity independent of the stimulation polarity.

Each of the atrial sensing circuit 82 or the ventricular sensing circuit 84 preferably employs one or more low power, precision amplifiers with programmable gain and automatic gain or sensitivity control, bandpass filtering, and a threshold detection circuit, to selectively sense the cardiac signal of interest. The automatic sensitivity control enables the stimulation device 11 to deal effectively with the difficult problem of sensing the low amplitude signal characteristics of atrial or ventricular fibrillation.

The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry, and the timing of any blocking circuitry coupled to the inputs of the atrial and ventricular sensing circuits 82 and 84.

For arrhythmia detection, the stimulation device 10 includes an arrhythmia detector 77 that utilizes the atrial and ventricular sensing circuits 82 and 84 to sense cardiac signals, for determining whether a rhythm is physiologic or pathologic. As used herein "sensing" refers to the process of noting an electrical signal. "Detection" refers to the step of confirming that the sensed electrical signal as the signal being sought by the detector. As an example, "detection" applies to the detection of both proper rhythms (i.e., "R wave" or "R wave") as well as improper dysrhythmias including arrhythmia and bradycardia (e.g., detection of the absence of a proper rhythm.)

The timing intervals between sensed events (e.g. P-waves, R-waves, and depolarization signals associated with fibrillation which are sometimes referred to as "F-waves" or "Fib-waves") are then classified by the arrhythmia detector 77 by comparing them to a predefined rate zone limit (e.g. bradycardia, normal, low rate ventricular tachycardia, high rate ventricular tachycardia, and fibrillation rate zones) and various other characteristics (e.g. sudden onset, stability, physiologic sensors, and morphology, etc.), in order to determine the type of remedial therapy that is needed (e.g. bradycardia pacing, anti-tachycardia stimulation, cardioversion shocks or defibrillation shocks, collectively referred to as "tiered therapy").

Cardiac signals are also applied to the inputs of a data acquisition system 90, which is depicted as an analog-to-digital (A/D) converter for simplicity of illustration. The data acquisition system 90 is configured to acquire intracardiac electrogram (EGM) signals or ECG signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch 74 to sample EGM signals across any pair of desired electrodes. Data acquisition system 90 is also coupled to electrodes 14 and 16 for sampling ECG signals for determining a heart rate.

Advantageously, the data acquisition system 90 may be coupled to the microcontroller 60 or another detection circuitry, for detecting an evoked response from the heart 12 in response to an applied stimulus, thereby aiding in the detection of "capture". In the embodiment shown in FIG. 7, the microcontroller 60 includes an automatic capture detector 65 that searches for an evoked response signal following a stimulation pulse during a "detection window" set by timing control circuitry 79. The microcontroller 60 enables the data acquisition system 90 via control signal 92 to sample the cardiac signal that falls in the capture detection window. The sampled signal is evaluated by automatic capture detector 65 to determine if it is an evoked response signal based on its amplitude, peak slope, morphology or another signal feature or combination of features. The detection of an evoked response during the detection window indicates that capture has occurred.

The microcontroller 60 is further coupled to a memory 94 by a suitable data/address bus 96, wherein the programmable operating parameters used by the microcontroller 60 are stored and modified, as required, in order to customize the operation of the stimulation device 11 to suit the needs of a particular patient. Such operating parameters define, for example, stimulation pulse amplitude, pulse duration, electrode polarity, rate, sensitivity, automatic features, arrhythmia detection criteria, syncope detection criteria, and the amplitude, waveshape and vector of each stimulation pulse to be delivered to the patient's heart 12 within each respective tier of therapy. Memory 94 is further capable of storing large amounts of physiological data in designated blocks of memory until such data is permanently downloaded to an external device 102.

Advantageously, the operating parameters of the stimulation device 11 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows an intracardiac electrogram (referred to as IEGM or EGM), stored physiologic signals, and status information relating to the operation of the stimulation device 11 (as contained in the microcontroller 60 or memory 94) to be sent to the external device 102 through the established communication link 104.

The stimulation device 11 further includes a physiologic sensor 108, commonly referred to as a "rate-responsive" sensor because it is typically used to adjust stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various stimulation parameters (such as rate, AV Delay, V—V Delay, etc.) at which the atrial and ventricular pulse generators 70 and 72 generate stimulation pulses.

In accordance with the present invention, physiologic sensor 108 includes one more sensors of physiological signals useful in the detection and diagnosis of vasovagal syncope. Thus, the physiological sensor 108 preferably includes a blood pressure sensor and a body posture sensor.

Microprocessor 60 is equipped with a syncope detector 79 for the detection of vasovagal syncope or pre-syncopal events using the physiological signals received from physiological sensor 108 and IEGM or ECG signals received from data acquisition system 90.

The stimulation device 11 additionally includes a power source such as a battery 110 that provides operating power to all the circuits shown in FIG. 7. For the stimulation device 11, which employs shocking therapy, the battery 110 must be capable of operating at low current drains for long periods of time, preferably less than 10 $\mu$A, and also be capable of providing high-current pulses when the patient requires a shock pulse, preferably, in excess of 2 A, at voltages above 2 V, for periods of 10 seconds or more. The battery 110 preferably has a predictable discharge characteristic so that elective replacement time can be detected.

The stimulation device 11 further includes a magnet detection circuitry 67 coupled to the microcontroller 60. The magnet detection circuitry detects when a magnet is placed over the stimulation device 11. A magnet may be used by a clinician to perform various test functions of the stimulation device 11 and/or to signal the microcontroller 60 via control signal 68 that the external programmer 102 is in place to receive or transmit data to the microcontroller 60 through the telemetry circuits 100. In accordance with the present invention a patient may hold a magnetic hand-held unit over the implanted device 11 when he or she feels symptomatic. Detection of a patient-activated signal by the magnet detection circuitry 67 results in a signal to the microcontroller 60 that heart rate and physiological signal data from physiologic sensor 108 should be acquired and stored in memory 94 for the purposes of diagnosing syncope or intermittent arrhythmias.

As further illustrated in FIG. 7, the stimulation device 11 is shown to include an impedance measuring circuit 112 which is enabled by the microcontroller 60 by control signal 114. In accordance with the present invention, the impedance measuring circuit 112 may be used to measure changes in body impedance using sensing electrodes 14 and 16 for the purposes of measuring a heart rate. Other known uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used.

If it is a function of the stimulation device 11 to operate as an implantable cardioverter/defibrillator (ICD) device, it must detect the occurrence of an arrhythmia, and automatically apply an appropriate electrical stimulation or shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high (11 to 40 Joules) energy, as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38 (FIG. 6). As noted above, the housing 40 may act as an active electrode in combination with the RV electrode 36, or as part of a split electrical vector using the SVC coil electrode 38 or the left atrial coil electrode 28.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

External device 102 is shown, in this embodiment, to include a control system 103 for controlling the programming and testing operations of the external device 102; a memory 105 for storing operational parameters or physiological data downloaded from stimulation device 11; a display 107 for displaying physiological data or results of issued programming commands; and a user interface 109 for entering programming commands or requests to retrieve data stored in stimulation device 11.

Figure 8:
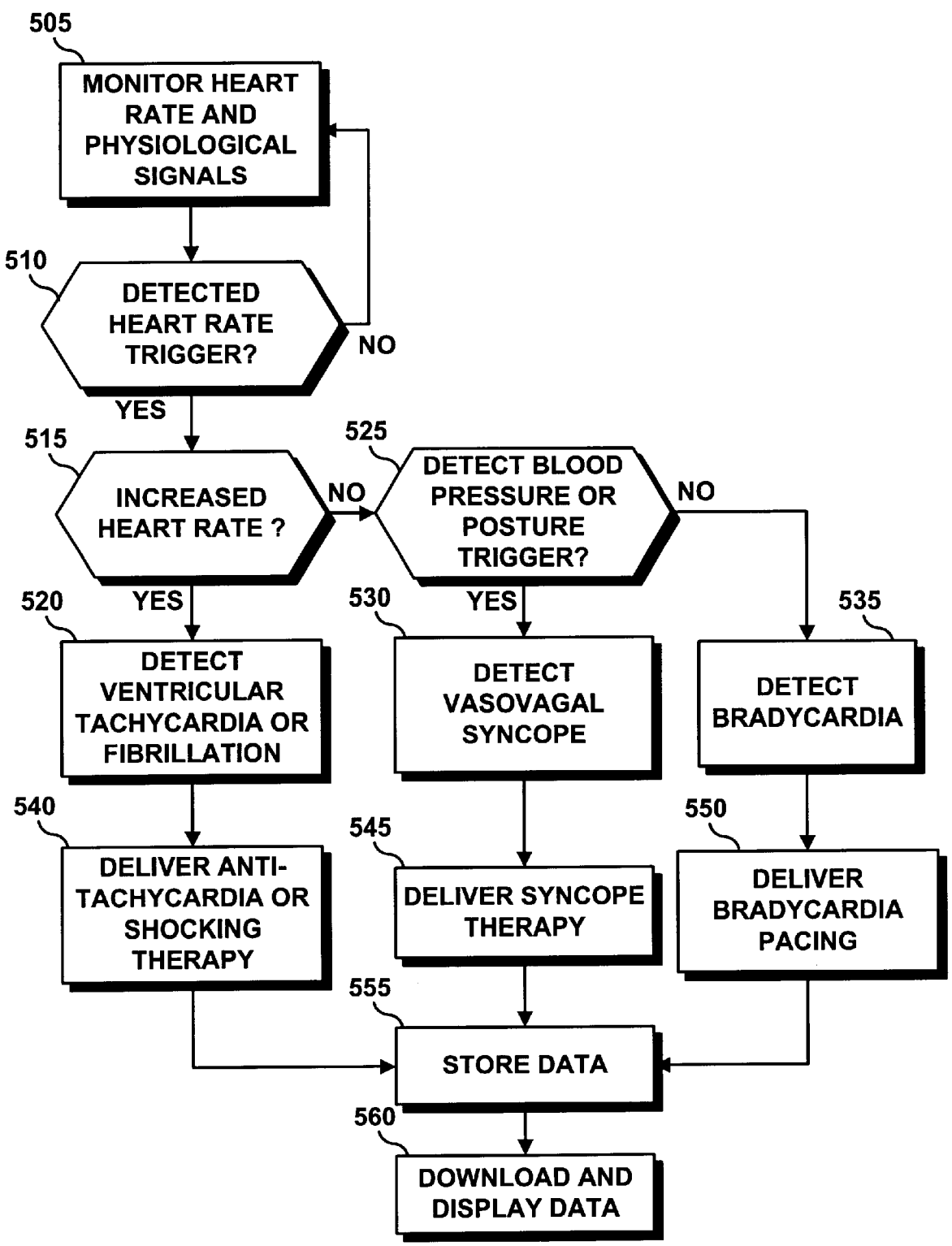
FIG. 8 is a flow chart providing an overview of the monitoring and treatment methods included in one embodiment of the stimulation device of FIG. 7 for the detection, diagnosis, and treatment of vasovagal syncope or cardiac arrhythmias.

In FIG. 8, a flow chart is shown depicting a method 500 included in one embodiment of the device 11 for detecting an arrhythmic or syncopal condition, acquiring and storing data leading up to and during a detected arrhythmia or syncopal event, and delivering a therapy for the detected condition. At step 505, the microprocessor 60 monitors the heart rate and other physiological data, preferably blood pressure and posture. At step 510, the microprocessor 60 determines if a trigger event based on heart rate has occurred, which may be a dramatic increase or decrease in heart rate or a detected rate above a maximum or below a minimum normal rate. Heart rate may be determined based on intervals between sensed cardiac events, such as P-waves or R-waves, obtained from IEGM signals sampled by data acquisition system 90. The heart rate may also be determined based on ECG signals measured from electrodes 14 and 16 or impedance measurements made by impedance measuring circuit 112 based on signals measured from electrodes 14 and 16. As long as no change is detected in heart rate, the device 11 continues to monitor the signals at step 505.

If a heart rate trigger is detected at decision step 510, the microprocessor 60 determines if it is an increase at step 515. An increase in heart rate is further analyzed by arrhythmia detector 77 at step 520 to determine the rate zone (low rate tachycardia, high rate tachycardia, or fibrillation) and confirm ventricular tachycardia or fibrillation. At step 540, the stimulation device 11 delivers stimulation or shocking therapy to terminate the detected tachycardia or fibrillation according to the programmed tiered-therapy operating parameters. Stimulation and shocking therapy may be enabled or disabled and, if enabled, delivered after all tachycardia or fibrillation detection criteria have been met. At step 555, heart rate and physiological data are written to memory 94 to record the arrhythmic episode for later downloading and display at step 560.

If a heart rate trigger detected at step 510 is due to a decrease in heart rate rather than an increase as determined at step 515, the syncope detector 79 further analyzes the blood pressure and/or body posture signals to determine if an additional trigger event based on these signals has occurred. For example, if a dramatic decrease in blood pressure is detected, vasovagal syncope may be confirmed at step 530. At step 545, a syncope therapy, if enabled, may be delivered by stimulation device 11. Typically, syncope is treated by delivering stimulation pulses at a rate higher than the intrinsic detected heart rate. At step 555, heart rate and other physiological data are written to memory 94 to record the syncopal episode and events preceding it. This data may then be downloaded and displayed at a later time at step 560.

If no additional trigger events based on the physiological sensors are detected by syncope detector 79 at decision step 525, for example blood pressure is in a normal range for the detected heart rate, then vasovagal syncope can not be confirmed and the reduction in heart rate is detected as bradycardia at step 535. Bradycardia pacing may be delivered at step 550 by the stimulation device 11 according to the programmed pacing mode and base rate. At step 555, the heart rate data and other physiological data (if desired) are written to memory 94 so that events leading up to and including the bradycardia episode are recorded and available for downloading and display at a later time at step 560.

Thus, a system and method for diagnosing vasovagal syncope or intermittent cardiac arrhythmias has been described in which physiological data is monitored and, when a detected trigger event occurs, stored in memory for later downloading and analysis by a physician. The methods described herein provide physiological data similar to tilt-table testing with the advantage of acquiring such diagnostic data during actual, spontaneous syncopal events. These methods may be included in a dedicated monitoring device, in a monitoring device capable of enabling a therapy method in another device, or in a therapeutic device that combines vasovagal syncope and arrhythmia monitoring with the delivery of appropriate therapy when such conditions are detected. While detailed descriptions of specific embodiments of the present invention have been provided, it would be apparent to those reasonably skilled in the art that numerous variations of the methods described herein are possible in which the concepts of the present invention may readily be applied. The descriptions provided herein are for the sake of illustration and are not intended to be exclusive.

What is claimed is:

1. A method of monitoring physiological signals comprising:
   acquiring at least a first and a second physiological signals;
   if the first physiological signal represents a blood pressure trigger event, determining a direction of change of the trigger event;
   if the direction of change of the trigger event represents a decrease in blood pressure, analyzing the second physiological signal to determine if a heart rate has changed since the decrease in blood pressure; and
   confirming a likelihood of vasovagal syncope if the heart rate does not increase.

2. The method of claim 1, further comprising, upon detection of the blood pressure trigger event, storing acquired physiological signals for a predetermined period.

3. The method of claim 2, further comprising displaying stored physiological data.

4. The method of claim 1, wherein acquiring the second physiological signal comprises acquiring an electrocardiogram (ECG) signal.

5. The method of claim 4, wherein acquiring the second physiological signal comprises acquiring heart rate measurement.

6. The method of claim 1, further comprising acquiring body posture measurement.

7. The method of claim 5, wherein acquiring heart rate measurement comprises detecting a maximum heart rate.

8. The method of claim 5, wherein acquiring heart rate measurement comprises detecting a minimum heart rate.

9. The method of claim 5, wherein acquiring heart rate measurement comprises detecting a predetermined change in the heart rate.

10. The method of claim 1, wherein analyzing the first physiological signal comprises detecting a maximum blood pressure.

11. The method of claim 1, wherein analyzing the first physiological signal comprises detecting a minimum blood pressure.

12. The method of claim 1, wherein analyzing the first physiological signal comprises detecting a predetermined change in blood pressure.

13. The method of claim 3, further comprising treating vasovagal syncope if vasovagal syncope is confirmed.

14. The method according to claim 13, wherein treating vasovagal syncope comprises delivering cardiac stimulation pulses at a rate above an intrinsic heart rate.

15. The method of claim 1, wherein selectively confirming vasovagal syncope comprises diagnosing intermittent cardiac arrhythmia.

16. The method according to claim 15, wherein confirming intermittent cardiac arrhythmia comprises confirming bradycardia.

17. The method according to claim 16, wherein confirming intermittent cardiac arrhythmia comprises confirming any one of low rate tachycardia, high rate tachycardia, and fibrillation.

18. The method of claim 16 further comprising treating the intermittent cardiac arrhythmia.

19. A device for monitoring physiological signals comprising:
   a plurality of sensors that acquire first and second physiological signals;
   a detector connected to at least one of the sensors, wherein the detector is operative to detect if the first physiological signal represents a blood pressure trigger event, and to determine a direction of change of the trigger event;
   a control circuit that analyzes the second physiological signal to determine if a heart rate has changed if the direction of change of the trigger event represents a decrease in blood pressure, wherein the circuit determines a potential vasovagal syncope condition exists if the heart rate has not increased.

20. The device of claim 19, wherein the second physiological signal comprises an electrocardiogram (ECG) signal.

21. The device of claim 20, wherein the second physiological signal comprises a heart rate measurement.

22. The device of claim 19, wherein the second physiological signal comprises a body posture measurement.

23. The device of claim 21, wherein the heart rate measurement comprises any one of:
   a maximum heart rate;
   a minimum heart rate; and
   a predetermined change in the heart rate.

24. The device of claim 19, wherein the control circuit analyzes the first physiological signal by analyzing any one of:
   a maximum blood pressure;
   a minimum blood pressure; and
   a predetermined change in blood pressure.

25. A cardiac stimulation device capable of monitoring physiological signals, the device comprising:
   means for detecting a blood pressure decrease;
   means for determining if a heart rate changes subsequent to the detected blood pressure decrease; and
   means for determining that a potential vasovagal syncope condition exists if the heart rate does not increase.

26. The device of claim 25, wherein the second physiological signal comprises an electrocardiogram (ECG) signal.

27. The device of claim 26, wherein the second physiological signal comprises a heart rate measurement.

28. The device of claim 25, wherein the second physiological signal comprises a maximum heart rate.

29. The device of claim 27, wherein the heart rate measurement comprises any one of:
   a maximum heart rate;
   a minimum heart rate; and
   a predetermined change in the heart rate.

30. The device of claim 25, wherein the control circuit analyzes the first physiological signal by analyzing any one of:
   a maximum blood pressure;
   a minimum blood pressure; and
   a predetermined change in blood pressure.

* * * * *